United States Patent [19]

Hensen et al.

[11] Patent Number: 5,609,167
[45] Date of Patent: Mar. 11, 1997

[54] ACIDIC HAIR CARE PREPARATIONS

[75] Inventors: Hermann Hensen, Haan, Germany; Dagmar Stuhrmann, Miami, Fla.; Oriol Ponsati Obiols; Esther Prat Queralt, both of Barcelona, Spain

[73] Assignee: Henkel Kommanditgesellschaft auf Aktien, Duesseldorf, Germany

[21] Appl. No.: 524,735

[22] Filed: Sep. 7, 1995

Related U.S. Application Data

[63] Continuation of Ser. No. 244,437, filed as PCT/EP92/02633, Nov. 16, 1992, abandoned.

[30] Foreign Application Priority Data

Nov. 25, 1991 [DE] Germany ............... 41 38 630.2

[51] Int. Cl.$^6$ ............... A61K 7/06; A61K 7/08
[52] U.S. Cl. ............... 132/202; 424/70.21; 424/70.24; 424/70.28
[58] Field of Search ............... 514/547, 552; 132/202; 424/70.21, 70.24, 70.28

[56] References Cited

FOREIGN PATENT DOCUMENTS

| | | |
|---|---|---|
| 0252441 | 1/1988 | European Pat. Off. |
| 0284036 | 9/1988 | European Pat. Off. |
| 0299787 | 1/1989 | European Pat. Off. |
| 0309052 | 3/1989 | European Pat. Off. |
| 0370675 | 5/1990 | European Pat. Off. |

OTHER PUBLICATIONS

Parf. Kosm. 56, 157 (1975).

*Primary Examiner*—Gary Geist
*Assistant Examiner*—Barbara S. Frazier
*Attorney, Agent, or Firm*—Ernest G. Szoke; Wayne C. Jaeschke; Real J. Grandmaison

[57] ABSTRACT

Described are acidic hair care agents containing quaternary fatty acid trialkanolamine ester salts of formula (I):

$$\{R^1CO-O-\{Z\}-\overset{\overset{\displaystyle CH_3}{|_+}}{N}-\{Z\}-O-OCR^1\} X^-, \\ | \\ \{Z\}-OH \qquad (I)$$

in which $R^1CO$ is a linear or branched aliphatic acylradical containing 6 to 22 carbon atoms and 0 or 1 double bond, $\{Z\}$ is an ethylene, propylene or isopropylene group and X is chloride, bromide, sulfate, methosulfate or phosphate. Such agents improve hair combability, have antistatic properties, arc easy to rinse out, impart an agreeable feel and have very little polluting action.

20 Claims, No Drawings

ACIDIC HAIR CARE PREPARATIONS

This application is a continuation of application Ser. No. 08/244,437 filed on Sep. 26, 1994, now abandoned, which is a 371 of PCT/EP92/02633, filed Nov. 16, 1992.

FIELD OF THE INVENTION

This invention relates to acidic hair-care preparations containing quaternized fatty acid trialkanolamine ester salts and to their use for the production of hair rinses, hair-care emulsions, hair tonics, aerosol foams and setting lotions.

PRIOR ART

Damage to the structure of hair is caused by frequent bleaching, permanent waving, dyeing, heavy UV exposure, washing with degreasing surfactants and normal ageing. The hair becomes brittle and loses its shine. In addition, the hair develops an electrostatic charge on combing, while the roughened surface of the hair gives rise to matting and knotting which make the hair difficult to comb. Accordingly, hair-care preparations with a combability-improving effect have acquired considerable significance on the cosmetics market. The preparations in question may be applied to the hair while it is still wet from washing, for example in the form of a rinse, an aerosol foam or even in the form of emulsions (cream rinses), and are either rinsed out after a contact time of a few minutes or are left on the hair.

Cationic surfactants, more particularly quaternary ammonium compounds, such as for example distearyl dimethyl ammonium chloride (DSDMAC), either on its own or in combination with various wax-like additives, such as hydrocarbons, fatty alcohols or fatty acid esters, have been successfully used as active substances for improving the structure of hair {Parf. Kosm. 56, 157 (1975)}.

Unfortunately, the cationic surfactants mentioned have the disadvantage of inadequate biodegradability, so that, after introduction into surface waters, they can gradually impair the ability of communities of aquatic organisms to function.

In addition, esters of betaine with fatty alcohols or fatty alcohol polyglycol ethers for use in acidic hair-care preparations are known from German patent application DE 35 74 A1. Although the betaine esters are ecologically safe, they are unsatisfactory in regard to combability improvement, antistatic effect, feel and rinsing behavior and, in addition, are not stable to hydrolysis in the acidic range.

Accordingly, the problem addressed by the present invention was to provide new hair-care preparations which would not have any of the disadvantages mentioned above.

DESCRIPTION OF THE INVENTION

The present invention relates to acidic hair-care preparations containing quaternized fatty acid trialkanolamine ester salts corresponding to formula (I):

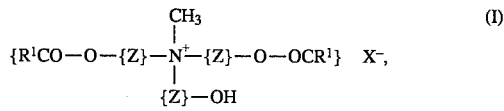

in which $R^1CO$ is a linear or branched aliphatic acyl radical containing 6 to 22 carbon atoms and 0 or 1 double bond, $\{Z\}$ is an ethylene, propylene or isopropylene group and X is chloride, bromide, sulfate, methosulfate or phosphate.

It has surprisingly been found that the preparations according to the invention can reduce the dry and wet combability of hair to 20% of the starting value and can almost completely suppress electrostatic charging on dry combing. The products provide the hair with a soft feel and are easy to rinse out. In contrast to typical market products, they are both aerobically and anaerobically completely biodegradable and are distinguished by unexpectedly slight acute and chronic toxicity to communities of aquatic organisms. In addition, they are extremely stable to hydrolysis and stable in storage both in the alkaline and in the acidic pH range.

Quaternized fatty acid trialkanolamine ester salts are known substances which may be obtained by the relevant methods of preparative organic chemistry. They may be produced, for example, from triethanolamine, which is esterified with fatty acids and then quaternized with dimethyl sulfate. The use of such compounds as fabric softeners is known, for example, from European patent application EP 0 370 675 A2.

Typical examples of quaternized fatty acid trialkanolamine ester salts are difatty acid esters of triethanolamine, tripropanolamine and tri-i-propanolamine with caproic acid, caprylic acid, captic acid, laurie acid, myristic acid, palmitic acid, stearic acid, oleic acid, elaidic acid, petroselic acid, arachic acid, behenic acid and erucic acid, which have been quaternized with methyl chloride, dimethyl sulfate or dimethyl phosphate. Preparations showing particularly favorable performance properties contain quaternized fatty acid trialkanolamine ester salts corresponding to formula (I) in which $R^1CO$ is a $C_{16-18}$ acyl radical, $\{Z\}$ is an ethylene group and X represents methosulfate.

As usual in oleochemistry, the technical fatty acid cuts obtained in the pressure hydrolysis of fats and oils, for example palm oil, palm kernel oil, coconut oil or beef tallow, may also be used for the production of the quaternized fatty acid trialkanolamine ester salts. Quaternized ester salts of which the fatty acid component is derived from $C_{12-18}$ and preferably $C_{16-18}$ fatty acids are preferred. In addition, quaternized ester salts produced from technical elaidic acid, i.e. an octadec-9-enoic acid containing 35 to 95% by weight and preferably 40 to 70% by weight of trans-double bonds, have proved to be particularly advantageous.

The preparations according to the invention may contain the ester salts corresponding to formula (I) in quantities of 0.1 to 25% by weight and preferably in quantities of 1 to 10% by weight, based on the preparation.

The pH value of the acidic hair-care preparations may be in the range from 2 to 5 and is preferably in the range from 2.5 to 4.5. It may be adjusted, for example, with acetic acid, lactic acid, citric acid, hydrochloric acid, phosphoric acid or betaine hydrochloride.

Although the preparations may even be marketed in the form of acidic solutions or suspensions of the quaternized fatty acid trialkanolamine ester salts in water, they preferably contain other components typical of cosmetic preparations, such as for example fatty alcohols, fatty alcohol polyglycol ethers, fatty acid esters, preservatives, vitamins and waxes.

The present invention also relates to the use of the fatty acid trialkanolamine ester salts corresponding to formula (I) for the production of hair-care preparations, such as for example hair rinses, hair-care emulsions, hair tonics, aerosol foams and setting lotions.

The following Examples are intended to illustrate the invention without limiting it in any way.

EXAMPLES

I. Quaternized fatty acid trialkanolamine ester salts used

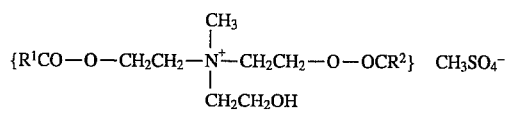

A1) $R^1CO=C_{16/18}$ acyl radical based on tallow fatty acid

A2) $R^1CO=C_{16/18}$ acyl radical based on palm oil fatty acid

A3) $R^1CO=C_{16/18}$ acyl radical based on technical elaidic acid: 40% by weight of trans-octadec-9-enoic acid 60% by weight of cis-octadec-9-enoic acid II. Formulations used

TABLE 1

Hair care formulations

| Components | Formulation | | | | |
|---|---|---|---|---|---|
| % by weight | A | B | C | D | E |
| A1 | — | — | 1.2 | — | — |
| A2 | — | — | — | 1.2 | — |
| A3 | — | — | — | — | 1.2 |
| Dehyquart DAM | — | 1.3 | — | — | — |
| Emulgade 1000 NI | 4.0 | 4.0 | 4.0 | 4.0 | 4.0 |
| Kathon CG | 0.07 | 0.07 | 0.07 | 0.07 | 0.07 |
| Water | | | ad 100 | | |
| pH value | | | 4.0 | | |

Legend:
Dehyquart ® DAM = distearyl dimethyl ammonium chloride
Emulgade ® 1000 NI = $C_{16/18}$ fatty alcohol/$C_{16/18}$ fatty alcohol 20 EO adduct (ratio by weight 1:1)
Kathon ® CG = preservative Formulations C, D and E correspond to the invention while formulations A and B are comparison formulations.

III. Application Examples a) Dry combability/electrostatic charging

Electrostatic charging was tested at the same time as dry combability with permitted electrostatic charging. A relative air humidity of 20% was established. The conditioning time was 12 h at 30° C. The measurement was carried out via the charge tap of a double Faraday cage after 10 combings. The measurement error was on average 2.5%; the statistical reliability was at least 99.9%. The results of the combing tests are set out in Tables 2 and 3.

b) Wet combability

Wet combability was tested on brown hair (Alkinco #6634, tress length 12 cm, tress weight 1 g). After the zero measurement, the tresses were soaked with 100 ml of formulations A to E. After a contact time of 5 minutes, the tresses were rinsed for 1 minute in running water (1 l/minute, 38° C.). The tresses were remeasured and compared with the zero measurement. The measurement error was on average 2%; the statistical reliability was at least 99%. The results are set out in Table 4.

A detailed description of the test methods can be found in J. Soc. Cosm. Chem., 24, 782 (1973).

TABLE 2

Dry combability

| Ex. | Formulation | Dry combability [mJ] | |
|---|---|---|---|
| | | Before | After |
| 1 | C | 4.5 | 0.8 |
| 2 | D | 4.0 | 0.7 |

TABLE 2-continued

Dry combability

| Ex. | Formulation | Dry combability [mJ] | |
|---|---|---|---|
| | | Before | After |
| 3 | E | 4.1 | 1.2 |
| C1 | A | 5.3 | 3.1 |
| C2 | B | 3.6 | 0.8 |

TABLE 3

Electrostatic charging

| Ex. | Formulation | Elstat. charging [V] | |
|---|---|---|---|
| | | Before | After |
| 4 | C | 1.8 | −0.2 |
| 5 | D | 2.1 | −0.2 |
| 6 | E | 2.2 | −0.1 |
| C2 | A | 2.5 | 1.2 |
| C3 | B | 2.2 | −0.2 |

TABLE 4

Wet combability

| Ex. | Formulation | Wet combability [mJ] | |
|---|---|---|---|
| | | Before | After |
| 7 | C | 24.0 | 7.3 |
| 8 | D | 23.6 | 4.5 |
| 9 | E | 20.9 | 4.9 |
| C5 | A | 27.4 | 18.5 |
| C6 | B | 23.7 | 3.8 |

We claim:

1. The process of treating human hair comprising contacting said hair with a hair care preparation consisting of:
   (a) quaternized fatty acid trialkanolamine ester salts corresponding to formula (I):

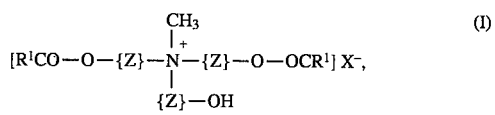

in which
   $R^1CO$ is a linear or branched aliphatic acyl radical containing 6 to 22 carbon atoms and not more than one double bond, {Z} is an ethylene, propylene or isopropylene group and
   X is chloride, bromide, sulfate, methosulfate or phosphate,
   (b) fatty alcohols, and
   (c) fatty alcohol polyglycol ethers.

2. A process as claimed in claim 1, wherein $R^1CO$ is an acyl radical containing 16 to 18 carbon atoms.

3. A process as claimed in claim 2, wherein {Z} is an ethylene group.

4. A process as claimed in claim 3, wherein X represents methosulfate.

5. A process as claimed in claim 4, wherein ester salts corresponding to formula (I) are present in quantities of 0.1 to 25% by weight, based on the preparation.

6. A process as claimed in claim 5, wherein the pH value of the preparation is in the range from 2 to 5.

7. A process as claimed in claim 1, wherein {Z} is an ethylene group.

8. A process as claimed in claim 1, wherein X represents methosulfate.

9. A process as claimed in claim 8, wherein ester salts corresponding to formula (I) are present in quantities of 0.1 to 25% by weight, based on the preparation.

10. A process as claimed in claim 7, wherein ester salts corresponding to formula (I) are present in quantities of 0.1 to 25% by weight based on the preparation.

11. A process as claimed in claim 3, wherein ester salts corresponding to formula (I) are present in quantities of 0.1 to 25% by weight, based on the preparation.

12. A process as claimed in claim 2, wherein ester salts corresponding to formula (I) are present in quantities of 0.1 to 25% by weight, based on the preparation.

13. A process as claimed in claim 1, wherein ester salts corresponding to formula (I) are present in quantities of 0.1 to 25% by weight, based on the preparation.

14. A process as claimed in claim 8, wherein the pH value of the preparation is in the range from 2 to 5.

15. A process as claimed in claim 11, wherein the pH value of the preparation is in the range from 2 to 5.

16. A process as claimed in claim 13, wherein the pH value of the preparation is in the range from 2 to 5.

17. A process as claimed in claim 4, wherein the pH value of the preparation is in the range from 2 to 5.

18. A process as claimed in claim 3, wherein the pH value of the preparation is in the range from 2 to 5.

19. A process as claimed in claim 2, wherein the pH value of the preparation is in the range from 2 to 5.

20. A process as claimed in claim 1, wherein the pH value of the preparation is in the range from 2 to 5.

\* \* \* \* \*